United States Patent [19]

Koziol

[11] Patent Number: 5,074,859

[45] Date of Patent: Dec. 24, 1991

[54] BEAM DELIVERY SYSTEM FOR CORNEAL SURGERY

[76] Inventor: Jeffrey E. Koziol, 1211 S. Arlington Heights Rd., Arlington Heights, Ill. 60005

[21] Appl. No.: 598,793

[22] Filed: Oct. 17, 1990

Related U.S. Application Data

[63] Continuation of Ser. No. 464,637, Jan. 5, 1990, abandoned, which is a continuation of Ser. No. 176,765, Apr. 1, 1988, abandoned.

[51] Int. Cl.$^5$ .............................................. A61N 5/02
[52] U.S. Cl. .......................................... 606/5; 606/17; 606/18; 128/395; 128/898
[58] Field of Search ........... 219/121.6, 121.73, 121.74, 219/121.76, 121.77, 121.79, 121.8, 121.84; 128/395, 397, 398, 898; 606/3, 4, 5, 17, 18

[56] References Cited

U.S. PATENT DOCUMENTS

| | | | |
|---|---|---|---|
| 3,821,510 | 6/1974 | Muncheryan | 219/121.79 |
| 3,931,491 | 1/1976 | Stumpf | 219/121.84 |
| 4,002,877 | 1/1977 | Banas | 214/121.84 |
| 4,028,525 | 6/1977 | Mominee et al. | 219/121.78 |
| 4,315,130 | 2/1982 | Inagaki et al. | 214/121.73 |
| 4,356,375 | 10/1982 | Josephy et al. | 214/121.73 |
| 4,370,540 | 1/1983 | Davis et al. | 219/121.6 |
| 4,409,979 | 10/1983 | Roussel et al. | 128/303.1 |
| 4,461,294 | 7/1984 | Baron | 128/303.1 |
| 4,518,232 | 5/1985 | Dagenais | 219/121.74 |
| 4,658,109 | 4/1987 | Honeycutt et al. | 219/121.73 |
| 4,665,913 | 5/1987 | L'Esperance, Jr. | 128/303.1 |
| 4,669,466 | 6/1987 | L'Esperance | 128/303.1 |
| 4,712,543 | 12/1987 | Baron | 128/303.1 |
| 4,720,619 | 1/1988 | Mattel et al. | 219/121.77 |
| 4,724,522 | 2/1988 | Beljorod | 128/303.1 |
| 4,729,372 | 3/1988 | L'Esperance | 219/121.74 |
| 4,732,148 | 3/1988 | L'Esperance, Jr. | 128/303.1 |

FOREIGN PATENT DOCUMENTS

| | | | |
|---|---|---|---|
| 2594686 | 8/1987 | France | 128/303.1 |
| 8707165 | 12/1987 | World Int. Prop. O. | 128/303.1 |

OTHER PUBLICATIONS

"Response of the Corneal Epithelium to KrF Excimer Laser Pulses", by J. Taboda et al.; Heath Physics, vol. 40 (May), pp. 677-683, 1981.

Primary Examiner—David Shay
Attorney, Agent, or Firm—Roylance, Abrams, Berdo & Goodman

[57] ABSTRACT

An apparatus and method for delivering radiant energy beams onto the cornea of an eye to ablate the cornea in a radial slot or lenticular pattern and thereby modify its curvature and refractive power. The apparatus includes an array of central reflectors and an assembly of peripheral reflectors. Each central reflector is associated with a respective peripheral reflector so that a beam reflected by the central reflector is intercepted by its associated peripheral reflector and is again reflected to precisely incise the cornea. In a modified embodiment, the assembly of peripheral reflectors and the array of central reflectors rotate to permit lathing of the cornea. Each peripheral reflector has a curved reflective surface to provide a line focus on the cornea.

24 Claims, 5 Drawing Sheets

BEAM DELIVERY SYSTEM FOR CORNEAL SURGERY

This is a continuation of application Ser. No. 07/464,637 filed Jan. 5, 1990 now abandoned, which application Ser. No. 07/464,637 is a continuation of Ser. No. 07/176,765 filed Apr. 1, 1988, now abandoned.

FIELD OF THE INVENTION

The invention relates to an apparatus for delivering radiant energy beams onto the cornea of an eye. More specifically, the invention relates to an array of central reflectors for intercepting a radiant energy beam and reflecting and splitting the beam along several paths to an assembly of peripheral reflectors radially spaced therefrom, which in turn focus and reflect the beams onto the cornea. The central reflector array and the peripheral reflector assembly can be rotated as a single unit relative to the eye for scanning operations. The invention when used in a stationary position can ablate the cornea via simultaneously applied radial incisions, and when rotated can re-profile the cornea via photolathing.

BACKGROUND OF THE INVENTION

The use of high intensity light sources such as lasers for cutting and reshaping eyes has expanded in recent years in part due to the superior precision, controllability and safety which such cutting technology offers over other cutting technologies, such as mechanical cutting of the eye. One type of ophthalmic surgical procedure for which high-intensity light radiation is particularly well suited is the radial keratotomy procedure in which a number of radial incisions are made on the cornea of the eye to change the curvature of the cornea.

Several methods and apparatus for performing radial keratotomies with lasers have been proposed. See, for example, U.S. Pat. No. 4,648,400 to Schneider et al; and U.S. Pat. No. 4,665,913 to L'Esperance, Jr. Schneider et al describe the use of lasers to selectively ablate the cornea of the eye by directing the laser beam through a generally planar mask having radial slots. The radial slots of the mask permit portions of the laser beam to pass through the mask and incise the cornea in a pattern of circumferentially spaced radial incisions.

Lasers have also been used to ablate an annular portion of the cornea by scanning or variably attenuating the laser beam. Such scanning changes the front surface of the cornea to a different optical curvature, thereby changing the refraction of the eye. See, for example, U.S. Pat. No. 4,669,466 to L'Esperance.

In such an application, it is desirable to deliver uniform beam energy along the curved scanning path. However, since the cornea presents a convexly curved surface to the laser beam, the outer circumferential portions of the cornea lie at further distances from the beam source than those portions at or near the center of the cornea. Thus, the laser beam incidents the cornea with a different angle along the cornea's constantly changing surface which causes variation of the energy density of the laser beam in a direction perpendicular to the corneal surface.

Using a mask to produce corneal incisions does not focus the beam on the corneal surface but merely projects the beam toward the surface.

Additionally, the energy of the laser beam may not be distributed uniformly due to the position of the mask relative to the beam. A non-uniform distribution of energy results in differing depths of the radial incisions, leading to an improper restructuring of the curvature of the cornea.

SUMMARY OF THE INVENTION

Accordingly, a primary object of the present invention is to provide an apparatus and method for delivering radiant energy from a radiant energy source onto a convex surface of the eye such that the energy density is substantially equal across all impacted portions of the eye.

A further object of the invention is to provide an apparatus and method which can simultaneously direct a number of radiant energy beams onto an eye from a single source.

A further object of the invention is to provide an apparatus and method which can direct radiant energy onto an eye so as to lathe the eye and form a lenticular ablation.

An additional object of the invention is to provide an apparatus and method for delivering radiant energy onto an eye which minimizes the energy needed to incise the cornea to a desired depth via focusing of the radiant energy.

Another object of the invention is to provide an apparatus and method for controlling radiant energy to produce optical changes in an eye and maintain substantially constant incision depth across the incision.

Another object of the invention is to provide an apparatus and method of conducting corneal surgery via focusing laser light and thus concentrate the laser energy 100 to 10,000 times to permit use of low cost lasers such as a frequency modified YAG laser.

The foregoing objects are basically attained by providing an apparatus for delivering radiant energy beams onto the cornea of an eye centered on an axis, the combination comprising a support, an array of central reflectors arranged about the axis for intercepting a beam incident thereon, each central reflector reflecting a portion of the incident beam, first means, coupled to said support and said array of central reflectors, for coupling said central reflectors to said support, an assembly of peripheral reflectors radially outwardly spaced from said central reflectors, each peripheral reflector arranged to intercept a reflected beam portion from an associated central reflector and to reflect said intercepted beam portion onto the cornea, and second means, coupled to said support and said peripheral reflectors, for coupling said peripheral reflectors to said support.

The foregoing objects are also attained by providing a method of ablating a cornea via a radiant energy beam comprising the steps of aligning a source of a radiant energy beam and the cornea along an axis, emitting the radiant energy beam from the source, splitting the beam into a plurality of beam portions and reflecting those beam portions radially of the axis, and reflecting the radially directed beam portions to produce output beam portions incident on the cornea.

Other objects, advantages and salient features of the invention will become apparent from the following detailed description, which, taken in conjunction with the annexed drawings, discloses preferred embodiments of the invention.

BRIEF DESCRIPTION OF THE DRAWINGS

Referring now to the drawings which form a part of this original disclosure.

DETAILED DESCRIPTION OF PREFERRED EMBODIMENTS

Figure 1:
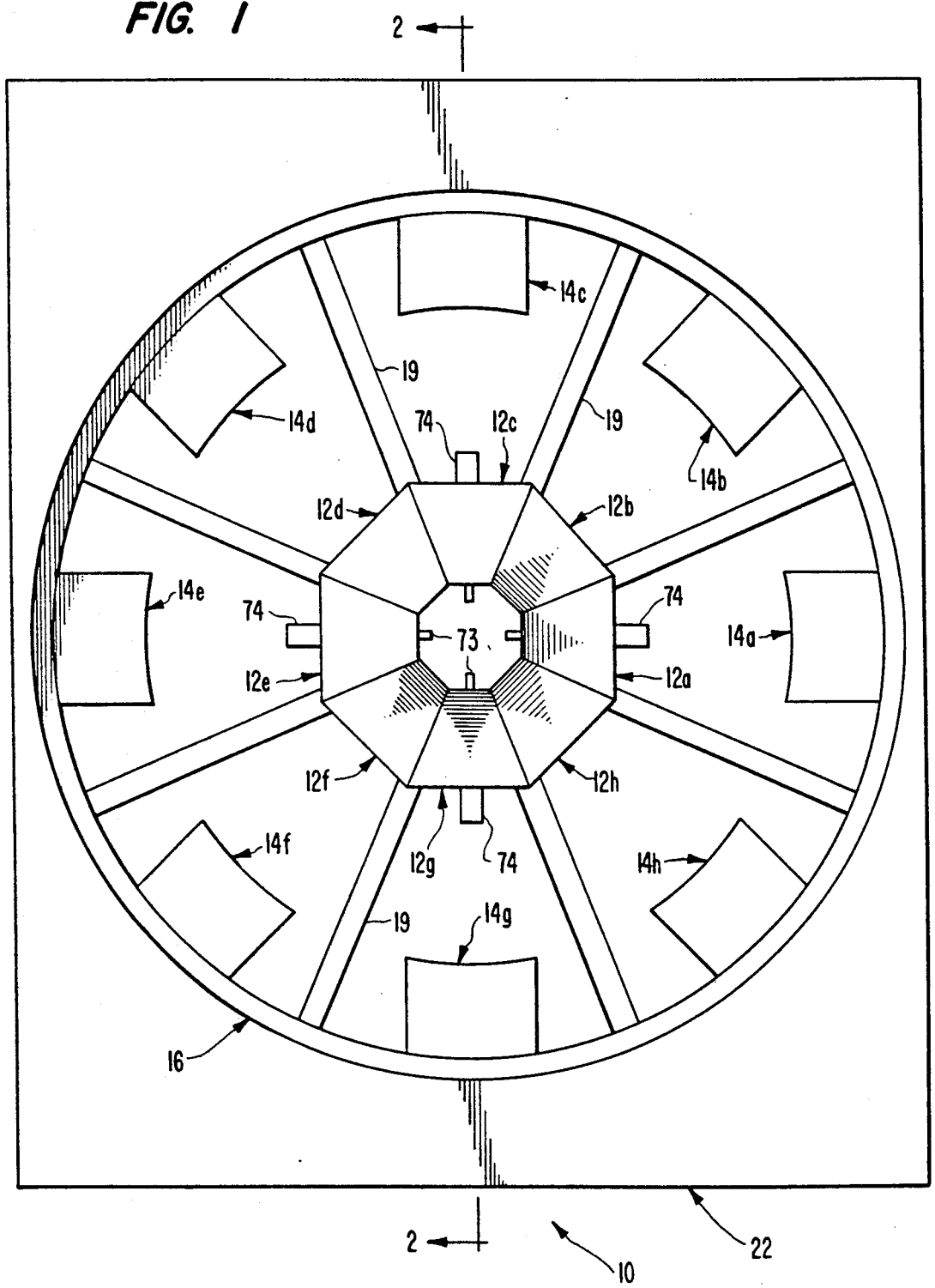
FIG. 1 is a front plan view of the beam delivering apparatus of the present invention, showing an array of central reflectors, each having an associated peripheral reflector radially and axially spaced from it.
Figure 2:
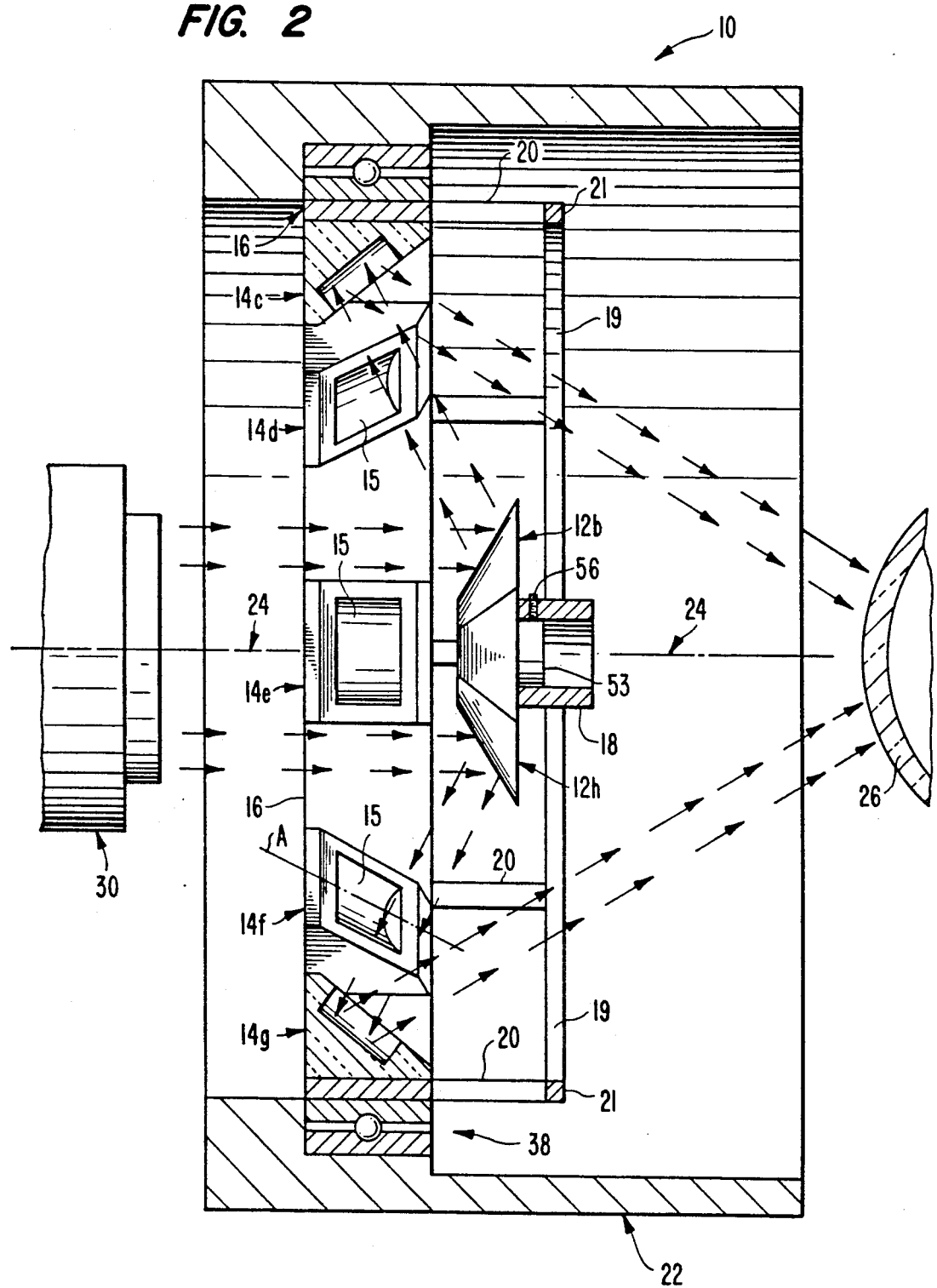
FIG. 2 is a cross-sectional side view of the beam directing apparatus of FIG. 1, taken along line 2—2 in FIG. 1 and showing the apparatus aligned between a laser beam source and the cornea of an eye.

As seen in FIG. 1, beam delivering apparatus 10 includes an annular array of central reflectors 12a-h and an annular assembly of peripheral reflectors 14a-h. Peripheral reflectors 14a-h are rigidly coupled to a rim 16. As seen in FIG. 2, rim 16 is rigidly coupled to a hub 18 by radial spokes 19, axial rods 20 and a ring 21. Central reflectors 12a-h are coupled to hub 18.

Beam delivering apparatus 10 is rotatably supported within a support or frame 22 about optical axis 24 which passes through the center of a cornea 26 of an eye. A laser beam source 30, such as a frequency modified YAG laser, is positioned to emit a beam along axis 24 and against central reflectors 12a-h. These reflectors split and reflect the beam onto peripheral reflectors 14a-h which then focus and reflect the split beams onto cornea 26.

Beam delivering apparatus 10 can be modified in a number of ways to adapt it for use in particular types of ophthalmic surgery. For example, beam delivering apparatus 10 can be modified to perform radial keratotomy operations on cornea 26.

Referring now more specifically to the construction and orientation of central reflectors 12a-h and peripheral reflectors 14a-h for the radial keratotomy operation, a number of equal sized central reflectors 12a-h are provided and, preferably, the number of central reflectors is an even number more than two and less than 16, such as eight. As shown in FIG. 1, eight equally sized central reflectors 12a-h are rigidly coupled to one another along their sides in an octagonal array. As seen in FIG. 2, each central reflector 12a-h is oriented to present a slanted, outwardly facing flat surface to the beam emanating from beam source 30. The angle of each surface is about 50°-60° to axis 24.

Each peripheral reflector 14a-h is associated with one of central reflectors 12a-h and is oriented so that its reflective surface 15, which is curved and preferably semi-cylindrical about central axis A as seen in FIG. 2 and angled at about 40°-50° to axis 24, intercepts the beam reflected radially by its associated central reflector. Axis A intersects axis 24 at an acute angle of about 40°-50°. Additionally, each peripheral reflector is oriented so as to reflect the intercepted beam axially and radially inward and to focus the beam into line focus onto cornea 26. The reflective surfaces of the central and peripheral reflectors can be mirrors or other reflective material.

Figure 6:
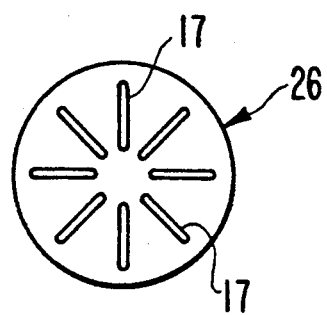
FIG. 6 is a schematic view of a cornea having radial incisions produced by a laser beam source in conjunction with the apparatus of FIGS. 1-3.

As schematically shown in FIG. 6, a number of radial incisions 17 are cut via photoablation in the cornea during the radial keratotomy operation. Beam delivering apparatus 10 can be used to produce the incisions simultaneously. As seen in FIG. 1, each central reflector 12a-h intercepts the beam and reflects the beam towards its associated peripheral reflector. Central reflectors 12a-h are preferably rotatably coupled to hub 18 via an axle 53 fitting into the hub 18 and a screw adjustment assembly including three set screws 56 to lock the reflectors relative to hub 18. Central reflectors 12a-h can be moved as a single unit relative to hub 18 and the adjustment screws 56 can then be operated to adjust and fix the relative position of the central reflectors relative to the peripheral reflectors. The combination of central and peripheral reflectors including the rim 16, hub 18, spokes 19, rods 20 and ring 21 are supported for rotation relative to frame 22 via ball bearing assembly 38, which is coupled to the frame and to rim 16. Thus, the angular position of the reflectors relative to the cornea and axis 24 can be varied. This allows angular placement as desired of the incisions 17 on the cornea.

The operation of beam delivering apparatus 10 during a simple radial keratotomy operation is as follows. Cornea 26 is immobilized by appropriate means and laser beam source 30 is positioned to emit a beam along axis 24, which passes through the center of cornea 26. Beam directing apparatus 10 is positioned between beam source 30 and cornea 26 and is appropriately spaced from cornea 26 so that the beams reflected by the central and peripheral reflectors ablate cornea 26 in the pattern comprising separate and discrete areas of ablation shown in FIG. 6. Once beam directing apparatus 10 is positioned, a test beam can be emitted to test the alignment of the beams on cornea 26. Beam source 30 is then operated to emit a radiant energy beam, such as a laser beam, which travels along axis 24, encounters the central reflectors 12a-h, is split and radially reflected against peripheral reflectors 14a-h and is then again radially reflected and focused onto cornea 26 to simultaneously make the incisions.

EMBODIMENT OF FIG. 3

Figure 3:
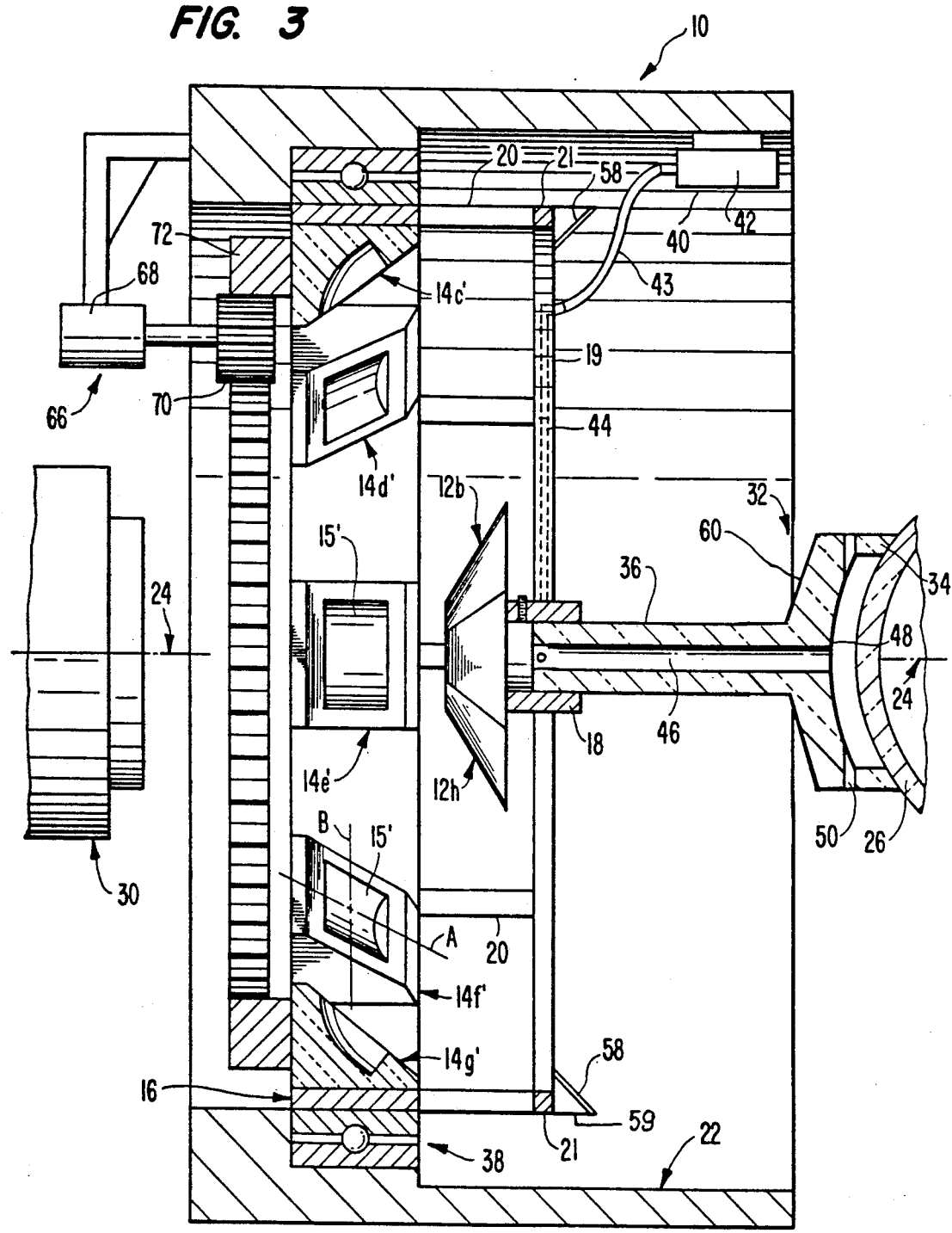
FIG. 3 is a cross-sectional side view of a modification of the apparatus of FIG. 1, having a gas conduit system for delivering gas to the ablated surface of the eye, a cornea alignment receptacle for positioning the cornea and a detection system for detecting the beam power density distribution as well as a motive assembly to rotate the reflectors.

With reference especially to FIG. 3, beam delivering system 10 can have added to it an eye positioning device 32, coaxial with axis 24 and coupled to hub 18. Eye positioning apparatus 32 has a concave surface 34, preferably having a radius of curvature the same as the average radius of curvature of a cornea, so that cornea 26 can be pressed against concave surface 34 and steadied in a fixed position during the eye operation. Eye positioning apparatus 32 is coupled via a connecting stem 36 to hub 18.

Eye positioning device 32 is preferably constructed of material which is transparent to the beam emitted by beam source 30 and permits complete through transmission of the beams reflected from the central and peripheral reflectors towards cornea 26.

Beam delivering apparatus 10 and eye positioning apparatus 32 can be provided with a gas or fluid conduit system 40 for delivering selected gases to the cornea 26 during ablation. Gas conduit system 40 includes a gas supply means 42 to supply gas along a tube 43 and a conduit 44 mounted within one of the spokes 19. Conduit 44 communicates with an axial conduit 46 within eye positioning apparatus 32 and axial conduit 46 communicates with a substantially semihemispheric recess 48 defined by concave surface 34. Recess 48 communicates with conduit 46 and cornea 26 and has outlets 50 for exhausting gases which have contacted cornea 26.

An inert gas such as argon can be supplied by gas conduit system 40 to contact cornea 26 and remove debris and other by-products of the surgical operation. Additionally, a gas or liquid having a cold temperature, such as, e.g., nitrous oxide, can be supplied by gas conduit system 40 to bathe cornea 26 in a cool environment and thereby lower the metabolic state of the cornea. Lowering the metabolic state of cornea 26 enhances the ability of the cornea to withstand traumatic insults from the beam.

To monitor the length and intensity of the beams directed onto cornea 26 by apparatus 10, a plurality of linear detector arrays 58 can be installed. As seen in FIG. 3, apparatus 32 includes frustoconical surface 60 adapted to partially reflect a small portion (about 5%) of the beams directed towards cornea 26 by peripheral reflectors. Surface 60 further reflects these small portions of the beams against linear detectors 58 which are coupled to a detector means 59 for determining the beam intensity distribution and length. Preferably, three detectors 58 are used, which are rigidly coupled to ring 21.

As seen in FIG. 3, the peripheral reflectors 14a'-h' are modified from those shown in FIGS. 1 and 2 by having a curved reflective surface 15' curved about an axis B which is perpendicular to axis A. This curvature about axis B approximates the curvature of the cornea being ablated and provides a more even ablation and beam intensity incident on the cornea. The radius of curvature of the reflective surface 15' about axis B reduces in the radially inward direction so the reflected line focus is substantially coincident with the outer surface of the cornea. Reflective surface 15' is also curved and preferably semi-cylindrical about axis A.

Beam delivering apparatus 10 of FIG. 3 therefore permits more precision in the radial keratotomy procedure than existing systems which interpose a mask between the beam source and the cornea. Unlike the beams produced by the existing systems, each portion of the beam reaching cornea 26 is substantially uniformly focused on the cornea in a curved line focus. Thus, the distribution of energy along the incision is substantially uniform and can therefore be more precisely controlled.

EMBODIMENT OF FIG. 4

Figure 4:
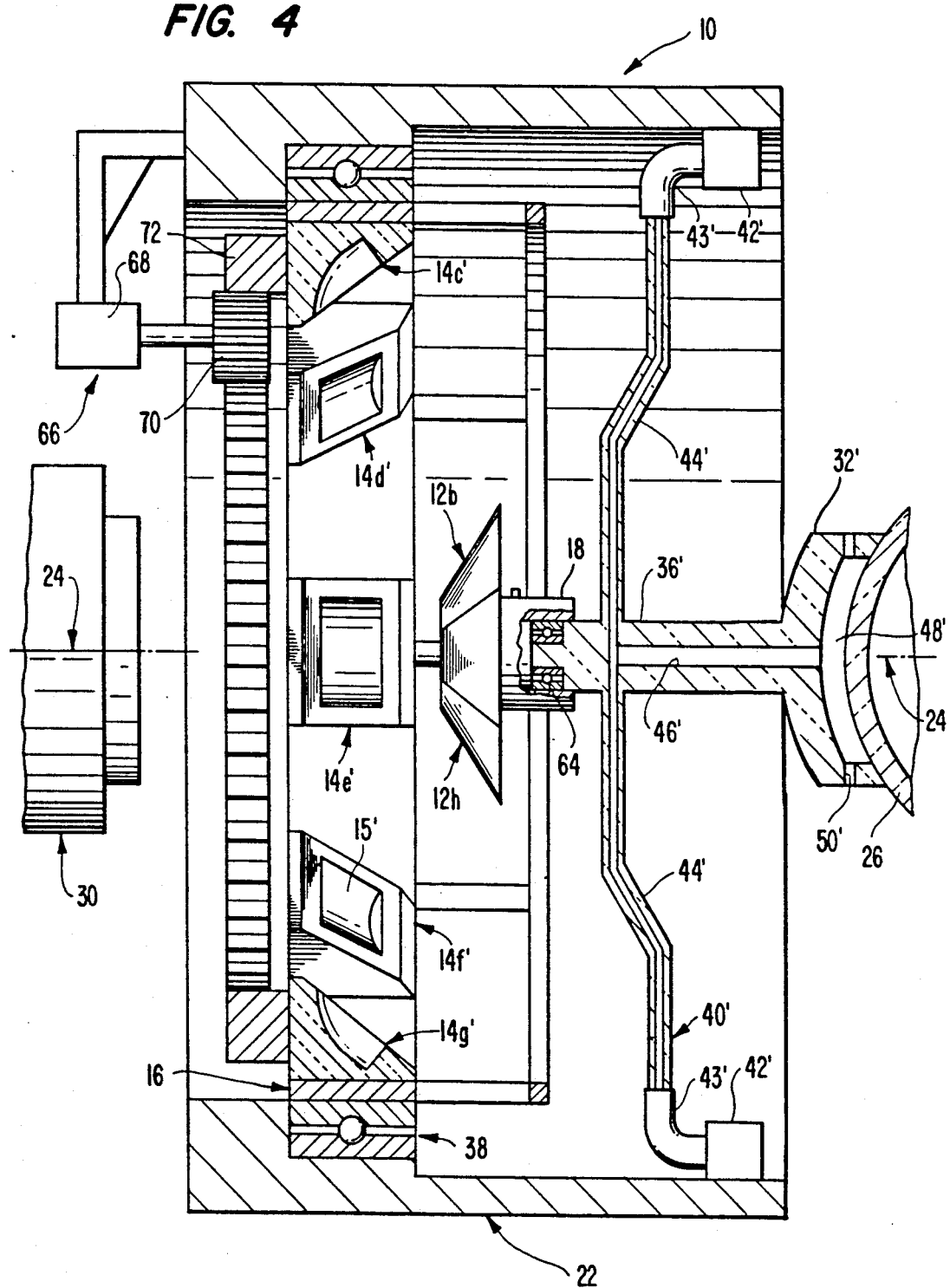
FIG. 4 is a cross-sectional side view of another modification of the apparatus of FIG. 1, showing a second gas conduit delivery system for delivering gas to the cornea of the eye during rotation of the reflectors.

With reference now to the use of beam delivering apparatus 10 in an eye lathing, or scanning, operation as shown in FIG. 4, apparatus 10 can be especially adapted for scanning an eye. In the embodiment shown in FIG. 4, gas conduit system 40' is constructed with its conduits 44' remote from spokes 20, in contrast to the embodiment shown in FIG. 3 in which conduit 44 is formed within one of the spokes 19. Ball bearing assembly 64 is provided at the connection of connecting stem 36' and hub 18 so that the central and peripheral reflectors can rotate relative to eye positioning device 32'. Additionally, a drive assembly 66 having a drive motor 68 for rotating a gear 70 is provided. Gear 70 meshes with a ring gear 72 which is rigidly connected to the sides of the peripheral reflectors.

Figure 7:
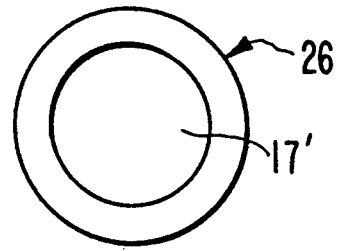
FIG. 7 is a schematic representation of a cornea having a lenticular ablation after scanning of radiant energy beams directed onto the cornea by the apparatus of FIG. 4.

To obtain the scanning pattern schematically shown in FIG. 7 as a full lenticular ablation, drive motor 68 is operated to rotate gear 70 which, in turn, rotates ring 72 to rotate reflectors 12a-h and 14a-h about axis 24. Preferably, the reflectors are rotated at a rate of approximately 200 revolutions per minute. However, rotation speed is preferably selected for the given beam focusing width on the cornea to remove material continuously over the cornea. Conduits 44' can be formed from plates or tubes which are transparent to the radiant energy beam so they do not interfere with the beam. The scanning incision 17' is shown in FIG. 7 and is in the form of a lenticular ablation in the shape of a positive, negative or toric lens. This ablation includes the full surface of the cornea, although a central part can be omitted, thereby providing an annular ablation. As used herein, "lenticular ablation" means removing corneal material via laser photoablation in the shape of an optical lens.

EMBODIMENT OF FIG. 5

Figure 5:
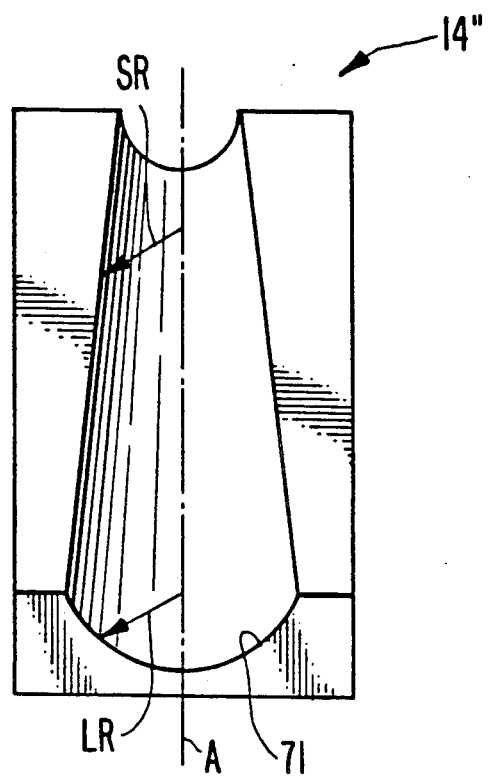
FIG. 5 is a perspective view of a modified peripheral reflector for use in the apparatus of FIG. 1, showing the change in the radius of curvature of the reflector along its central axis A.

To more precisely tailor the curved line focus of the beams reflected from the peripheral reflectors so that corneas of differing radii of curvature can be accommodated, each peripheral reflector can be designed with a curved reflective surface whose curvature varies along the length of the reflector along central axis A. As shown in FIG. 5, peripheral reflector 14" has a concave surface 71 varying from a smaller radius SR to a larger radius LR. Accordingly, the beams reflected onto the cornea 26 from reflector 14" produces radial incisions of desired curved line focus and thus intensity therealong. Reflector 14" accomplishes a similar result as reflectors 14a'-h' as seen in FIG. 3 but via a different reflector configuration.

As shown in FIG. 1, the central reflectors can also be provided with four inner and four outer alignment detectors 73 and 74 which monitor the alignment of the reflectors with respect to the beam incident thereon to allow adjustment of the laser beam to the optical center thereof.

The beam delivering apparatus 10 of the present invention controls and focuses the beam on the corneal surface. This is beneficial since the greater the amount of energy radiated onto the cornea, the greater the risk that the cornea will be damaged by overheating or, in the case of ultraviolet radiation, by overshock.

The overall delivery system is quite compact and can be enclosed between the laser 30 and gas conduit system 40' shown in FIG. 4. This allows filling of the whole beam delivering system with a neutral gas to minimize ozone build-up by ultraviolet radiation.

As seen by comparing FIGS. 2 and 4, the arrangement of the central and peripheral reflectors is the same for radial keratotomy and lathing via scanning. The only difference in these procedures is the rotation of the central and peripheral reflectors during scanning.

While various advantageous embodiments have been chosen to illustrate the invention, it will be understood by those skilled in the art that various changes and modifications can be made therein without departing from the scope of the invention as defined in the appended claims.

What is claimed is:

1. An apparatus for delivering radiant energy beams onto the cornea of an eye centered on a main optical axis, the combination comprising:

a source of a radiant energy beam aimed along the main optical axis;

a support;

an array of discrete central reflector means, arranged about the main optical axis, for intercepting the radiant energy beam incident thereon, splitting the beam into a plurality of beam portions, and reflecting each beam portion outwardly of the main optical axis;

first means, coupled to said support and said array of central reflector means, for coupling said central reflector means to said support;

an assembly of discrete peripheral reflector means, outwardly spaced from said central reflector means, each peripheral reflector means for intercepting one of said reflected beam portions from an associated central reflector means and for directing said intercepted beam portion generally along the main optical axis and incident onto the cornea; and second means, coupled to said support and said peripheral reflector means, for coupling said peripheral reflector means to said support, each of said peripheral reflector means including means for focusing said intercepted beam portion onto an area on the cornea separate and discrete from the incidence of the other of said intercepted beam portions on the cornea and in a line configuration extending outwardly from the main optical axis in the radial direction.

2. An apparatus as claimed in claim 1, wherein said second means comprises means for supporting said array of central reflector means for angular movement relative to said assembly of peripheral reflector means.

3. An apparatus as claimed in claim 1, wherein said first and second means comprises means, coupled to said array of central reflector means and said assembly of peripherally reflector means, for fixedly interconnecting said array and said assembly, and means for rotatably supporting said interconnected array and assembly on said support for rotation about the main optical axis, and means for rotating said interconnected array and assembly.

4. An apparatus as claimed in claim 1, wherein said central reflector means are mirrors.

5. An apparatus as claimed in claim 1, wherein said peripheral reflector means are mirrors.

6. An apparatus as claimed in claim 1, wherein said central reflector means have flat reflective surfaces.

7. An apparatus as claimed in claim 1, wherein said array of central reflector means is an annular array.

8. An apparatus as claimed in claim 1, wherein each of said means for focusing comprises a curved reflective surface.

9. An apparatus as claimed in claim 1, wherein each of said means for focusing comprises a substantially semi-cylindrical reflective surface.

10. An apparatus as claimed in claim 1, wherein said assembly of peripheral reflector means is an annular assembly.

11. An apparatus as claimed in claim 1, wherein each of said means for focusing comprises a reflective surface that is curved about an axis A and is curved about an axis B which is perpendicular to axis A.

12. An apparatus as claimed in claim 1, wherein each of said means for focusing comprises a reflective surface that is curved about an axis A, the radius of curvature varying therealong.

13. An apparatus as claimed in claim 1, and further comprising means, coupled to said support, for cooling the cornea.

14. An apparatus as claimed in claim 1, wherein said array of central reflector means includes from two to eight central reflector means, and said assembly of peripheral reflector means includes from two to eight peripheral reflector means.

15. An apparatus as claimed in claim 1, wherein said array of central reflector means is an octagonal array.

16. An apparatus as claimed in claim 1, and further comprising means, coupled to said support, for reflecting a part of the beams reflected by said peripheral reflector means and determining the length of the beam from the source and the energy distribution of the beams.

17. An apparatus as claimed in claim 1, and further comprising an eye positioning device coupled to said support for positioning the cornea relative to said central reflector means.

18. An apparatus as claimed in claim 17, and further comprising conduit means coupled to said eye positioning device for delivering fluid to the cornea.

19. A method of ablating a cornea via a radiant energy beam comprising the steps of aligning a source of radiant energy beam and the cornea along a main axis, emitting the radiant energy beam from the source, splitting the beam into a plurality of beam portions and reflecting those beam portions outwardly of the main axis, and reflecting the outwardly directed beam portions generally along the main axis to produce output beam portions and directing and focusing each of the output beam portions for incidence on the cornea in an area separate and discrete from the incidence of the other of the output beam portions on the cornea and in a line configuration extending outwardly from the main axis in the radial direction.

20. A method according to claim 19, wherein the first reflecting step also includes the step of reflecting the beam portions away from the cornea.

21. A method according to claim 19, wherein the splitting and first and second reflecting steps include the step of angularly aligning the output beam portions relative to the cornea.

22. A method according to claim 19, wherein the splitting, the two reflecting, and the directing and focusing steps include the step of revolving the output beam portions about the main axis.

23. A method as claimed in claim 19, wherein the second reflecting step includes focusing the output beam portions in a curved line configuration on the cornea.

24. A method as claimed in claim 23, wherein the splitting, the two reflecting, and the directing and focusing steps include the step of revolving the output beam portions about the main axis.

* * * * *

UNITED STATES PATENT AND TRADEMARK OFFICE
CERTIFICATE OF CORRECTION

PATENT NO. : 5,074,859
DATED : December 24, 1991
INVENTOR(S) : Jeffrey E. Koziol It is certified that error appears in the above-identified patent and that said Letters Patent is hereby corrected as shown below:

In the claims, column 7, line 48, "peripherally" should read -- peripheral --. Column 8, line 30, "beam" should read -- beams --.

Signed and Sealed this

Twenty-fifth Day of May, 1993

Attest:

MICHAEL K. KIRK

*Attesting Officer*    Acting Commissioner of Patents and Trademarks